(12) United States Patent
Cheng

(10) Patent No.: US 12,048,451 B2
(45) Date of Patent: Jul. 30, 2024

(54) ULTRASONIC SCALPEL

(71) Applicant: Shenzhen Channel Medical Equipment Co., Ltd., Guangdong (CN)

(72) Inventor: Yan Cheng, Guangdong (CN)

(73) Assignee: Shenzhen Channel Medical Equipment Co., Ltd., Guangdong (CN)

( * ) Notice: Subject to any disclaimer, the term of this patent is extended or adjusted under 35 U.S.C. 154(b) by 0 days.

(21) Appl. No.: 18/075,164

(22) Filed: Dec. 5, 2022

(65) Prior Publication Data

US 2023/0389953 A1    Dec. 7, 2023

(30) Foreign Application Priority Data

Jun. 1, 2022 (CN) .......................... 202210616772.2

(51) Int. Cl.
*A61B 17/32* (2006.01)
*A61B 17/00* (2006.01)

(52) U.S. Cl.
CPC ............... *A61B 17/320068* (2013.01); *A61B 2017/00862* (2013.01); *A61B 2017/320074* (2017.08); *A61B 2017/320082* (2017.08)

(58) Field of Classification Search
CPC ........... A61B 2017/320075; A61B 17/320068; A61B 17/3211–3213; A61B 17/285; A61B 2017/320082; A61B 2018/00589
See application file for complete search history.

(56) References Cited

U.S. PATENT DOCUMENTS

| | | | | |
|---|---|---|---|---|
| 5,769,211 A * | 6/1998 | Manna | ........... | A61B 17/320068 |
| | | | | 200/549 |
| 6,572,554 B2 * | 6/2003 | Yock | ................. | A61B 5/02007 |
| | | | | 600/463 |
| 6,623,500 B1 * | 9/2003 | Cook | ................. | A61B 18/1402 |
| | | | | 702/106 |
| 2011/0196404 A1 * | 8/2011 | Dietz | ............... | A61B 17/22004 |
| | | | | 606/169 |
| 2012/0116261 A1 * | 5/2012 | Mumaw | ................. | G16H 20/40 |
| | | | | 601/2 |

FOREIGN PATENT DOCUMENTS

| | | | | | |
|---|---|---|---|---|---|
| CN | | 109009333 A | * | 12/2018 | ...... A61B 17/320068 |
| EP | | 3607900 A1 | * | 2/2020 | ...... A61B 17/320068 |
| WO | WO-2022095726 A1 | * | 5/2022 | ...... A61B 17/320068 |

OTHER PUBLICATIONS

WO 2022095726 A1 English Translation via Espacenet (Year: 2022).*
CN-109009333-A Translation via Espacenet (Year: 2018).*

\* cited by examiner

*Primary Examiner* — Katherine H Schwiker
*Assistant Examiner* — Zehra Jaffri
(74) *Attorney, Agent, or Firm* — Quarles & Brady LLP

(57) ABSTRACT

An ultrasonic scalpel includes a scalpel body, a scalpel rod, and an ultrasonic generator, where an annular conductive part, the ultrasonic generator, and an elastic conductive part are arranged in the scalpel body; the scalpel rod is connected to an output terminal of the ultrasonic generator; and the annular conductive part and the scalpel body are connected to each other. An intermediate shell is arranged to fixedly engage with an outer side of the ultrasonic generator; a mounting hole which fits the elastic conductive part is provided in an outer side of the intermediate shell; and the elastic conductive part is electrically connected to the ultrasonic generator and the annular conductive part respectively.

7 Claims, 4 Drawing Sheets

ULTRASONIC SCALPEL

CROSS-REFERENCE TO RELATED APPLICATION

This application is filed on the basis of Chinese patent application No. 202210616772.2 filed Jun. 1, 2022, and claims priority of the Chinese patent application, the entire contents of which are incorporated herein by reference.

TECHNICAL FIELD

The disclosure relates to the technical field of medical devices, in particular to an ultrasonic scalpel.

BACKGROUND

Ultrasonic scalpels, as high-frequency electrosurgical units, are mainly used for biological tissue cutting, blood-vessel closure, and other operations. The ultrasonic scalpels have the features of less blood loss, less damage to surrounding tissues, faster postoperative recovery, and the like. They play a role of cutting and coagulation when applied to human tissues without causing side effects such as tissue dehydration and tissue burn. Even during the operation of scalpel blades, no current flows through human bodies. Therefore, the ultrasonic scalpels are widely used in operating rooms and are called bloodless scalpels.

The ultrasonic scalpels generally includes an ultrasonic host and a scalpel handle. An ultrasonic generator is mounted in the scalpel handle. The ultrasonic generator and the ultrasonic host may be connected by means of electric wires, and the connection here refers to the direction connection of positive and negative electrodes of the ultrasonic generator with respective positive and negative electrodes of the external electric wires. Moreover, when the angle of a scalpel blade needs to be adjusted, the scalpel handle is directly rotated to achieve the rotation of the scalpel blade, so as to complete operation.

However, in the existing technology, the ultrasonic generator, electric wires within the scalpel rod, and external electric wires are relatively fixed to one another. As a result, when the angle of the scalpel blade is adjusted, the external electric wires will be wound, decreasing the control accuracy of operators on the scalpels, and thus affecting the success rate of operations.

SUMMARY

In view of the above, the objective of the disclosure is to provide an ultrasonic scalpel to address the technical problem in the existing technology that the ultrasonic generator, electric wires within the scalpel rod, and external electric wires are relatively fixed to one another, and the external electric wires will be wound when the angle of the scalpel blade is adjusted, decreasing the control accuracy of operators on the scalpels, and thus affecting the success rate of operations.

To achieve the above objective, the disclosure provides the following technical solution. An ultrasonic scalpel includes a scalpel body, a scalpel rod, and an ultrasonic generator. An annular conductive part, the ultrasonic generator, and an elastic conductive part are arranged in the scalpel body. The scalpel rod is connected to an output terminal of the ultrasonic generator. The annular conductive part and the scalpel body are connected to each other. An intermediate shell is arranged to fixedly engage with an outer side of the ultrasonic generator. A mounting hole which fits the elastic conductive part is provided in an outer side of the intermediate shell. The elastic conductive part is electrically connected to the ultrasonic generator and the annular conductive part respectively.

By the above technical solution, positive and negative electrodes of the ultrasonic generator are welded to the elastic conductive part; the elastic conductive part penetrates through the intermediate shell to be connected to the annular conductive part; and a scalpel blade is electrically connected to the elastic conductive part. Therefore, when a rear shell is rotated, a 360-degree electrical conduction between the ultrasonic generator and the scalpel blade can be better fulfilled, so that the external electric wires are prevented from being wound, achieving the convenience in use. Accordingly, an operator can better operate the ultrasonic scalpel, greatly improving a success rate of an operation.

In some embodiments, the annular conductive part includes a first conductive ring and a second conductive ring; the scalpel body is internally provided with two clamping grooves in cooperation with the first conductive ring and the second conductive ring respectively.

By the above technical solution, by means of the first conductive ring and the second conductive ring, electrical conduction is facilitated. By means of the clamping grooves, mounting of the first conductive ring and the second conductive ring is facilitated, so that a task can be better completed.

In some embodiments, the elastic conductive part includes a spring needle or leaf spring for connecting the annular conductive part to the ultrasonic generator.

By the above technical solution, by means of the spring needle or leaf spring, the connection between the annular conductive part and the ultrasonic generator is facilitated, so that current output is facilitated.

In some embodiments, a handle is arranged on an outer side of the scalpel body; and the handle is configured for holding the scalpel body by a hand.

By the above technical solution, performability of the ultrasonic scalpel is ensured.

In some embodiments, a rear shell and a front shell which fit the ultrasonic generator are arranged in the scalpel body, and the rear shell and the front shell are both configured for sealing the ultrasonic generator.

By the above technical solution, the ultrasonic generator is sealed for protection, thereby prolonging the service life of the ultrasonic generator.

In some embodiments, a mounting groove which fits the ultrasonic generator is provided in an inner wall of the intermediate shell, and the mounting groove is configured for limiting the ultrasonic generator.

By the above technical solution, mounting of the ultrasonic generator is facilitated to limit radial motion of the ultrasonic generator, so as to ensure normal operation of the ultrasonic scalpel.

In some embodiments, a scalpel blade in cooperation with a handle is arranged at a tail end of the scalpel rod, and the scalpel blade is electrically connected to the elastic conductive part.

By the above technical solution, better transmission from the ultrasonic generator to the scalpel blade is facilitated, so as to complete the task.

In conclusion, the disclosure mainly has the following beneficial effects. By provision of the annular conductive part, the elastic conductive part, and other structures, when in use, the positive and negative electrodes of the ultrasonic generator are welded to the elastic conductive part; the elastic conductive part penetrates through the intermediate shell to be connected to the annular conductive part; and the annular conductive part are electrically connected to the external electric wires, so that the 360-degree electrical conduction between the ultrasonic generator and the external electric wires can be fulfilled. Therefore, when the angle of the scalpel blade needs to be adjusted, it is only necessary to rotate the rear shell, which is simple and rapid and prevents the external electric wires from being wound, so that the control degree of the operator is enhanced, thereby improving the success rate of the operation.

Figure 1:
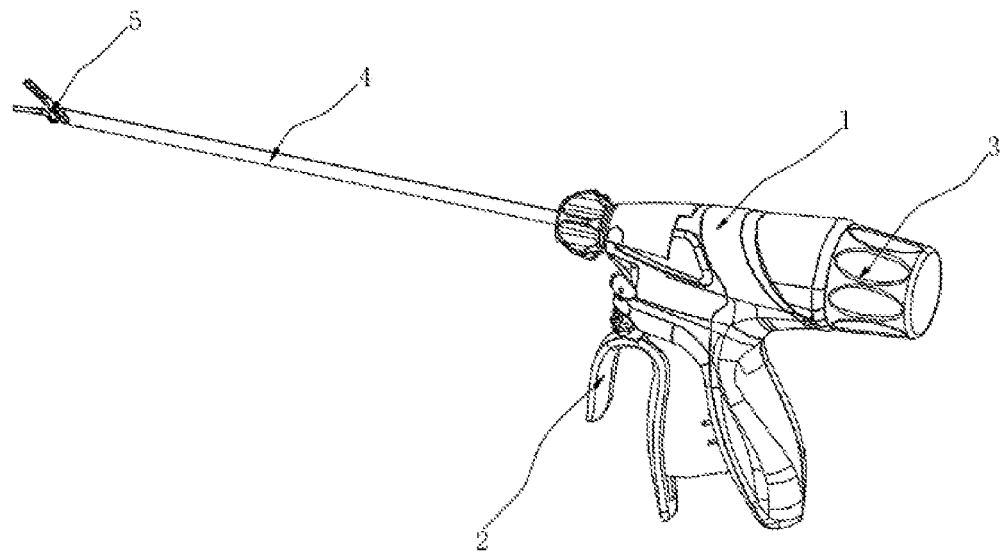
FIG. 1 is a schematic structural view of the disclosure.

Reference numerals: 1, scalpel body; 2, handle; 3, rear shell; 4, scalpel rod; 5, scalpel blade; 6, clamping groove; 7, first conductive ring; 8, second conductive ring; 9, intermediate shell; 10, front shell; 11, elastic conductive part; 12, ultrasonic generator; 13, mounting hole.

DETAILED DESCRIPTION

The technical solutions in the embodiments of the disclosure will be clearly and completely described below with reference to the accompanying drawings in the embodiments of the disclosure. The embodiments described below with reference to the accompanying drawings are exemplary, and are merely intended to illustrate the disclosure, rather than to limit the disclosure.

The embodiments of the disclosure are described below according to an overall structure of the disclosure.

As shown in FIG. 1 to FIG. 6, an ultrasonic scalpel includes a scalpel body 1, a scalpel rod 4, and an ultrasonic generator 12. An annular conductive part, the ultrasonic generator 12, and an elastic conductive part 11 are arranged in the scalpel body 1. The scalpel rod 4 is connected to an output terminal of the ultrasonic generator 12. The annular conductive part and the scalpel body 1 are connected to each other. An intermediate shell 9 fixedly engages with an outer side of the ultrasonic generator 12. Mounting holes 13 which fit the elastic conductive part 11 are provided in an outer side of the intermediate shell 9. Positive and negative electrodes of the ultrasonic generator are welded to the elastic conductive part 11. The elastic conductive part 11 penetrates through the intermediate shell 9 to be respectively connected to the annular conductive part. The elastic conductive part 11 is electrically connected to the ultrasonic generator 12 and the annular conductive part, respectively. A scalpel blade 5 is electrically connected to the elastic conductive part. Therefore, when a rear shell 3 is rotated, a 360-degree electrical conduction between the ultrasonic generator 12 and the scalpel blade 5 can be better fulfilled, so that the external electric wires are prevented from being wound, achieving the convenience in use. Accordingly, an operator can better operate the ultrasonic scalpel, greatly improving a success rate of an operation.

Referring to FIG. 2, FIG. 4, FIG. 5, and FIG. 6, the annular conductive part includes a first conductive ring 7 and a second conductive ring 8. By means of the first conductive ring 7 and the second conductive ring 8, the electrical conduction is facilitated. The first conductive ring 7 and the second conductive ring 8 respectively fit clamping grooves 6, and two clamping grooves 6 are provided in the scalpel body 1. By means of the clamping grooves 6, mounting of the first conductive ring 7 and the second conductive ring 8 is facilitated, so that a task can be better completed.

Figure 2:
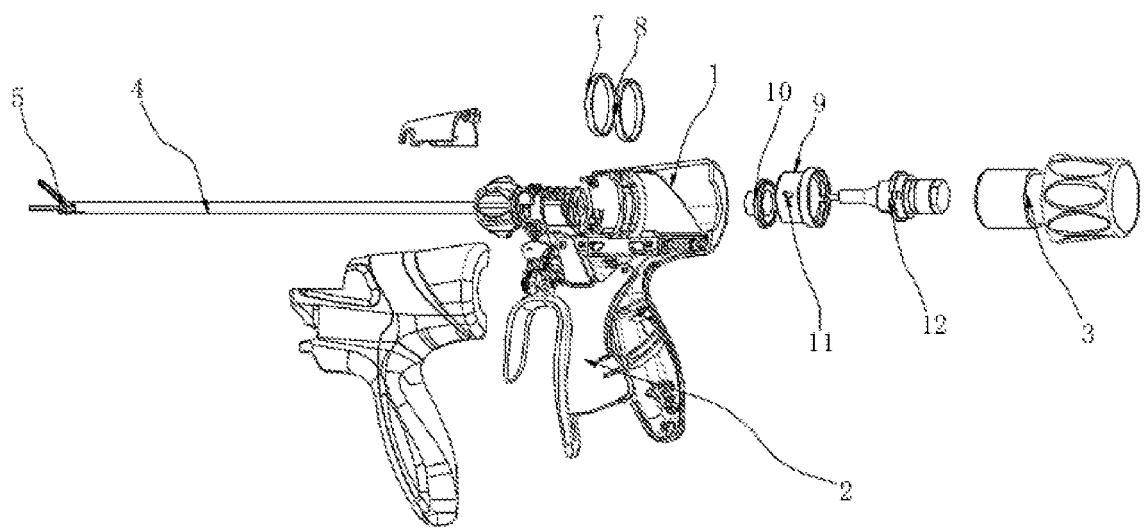
FIG. 2 is an exploded structural view of the disclosure.
Figure 3:
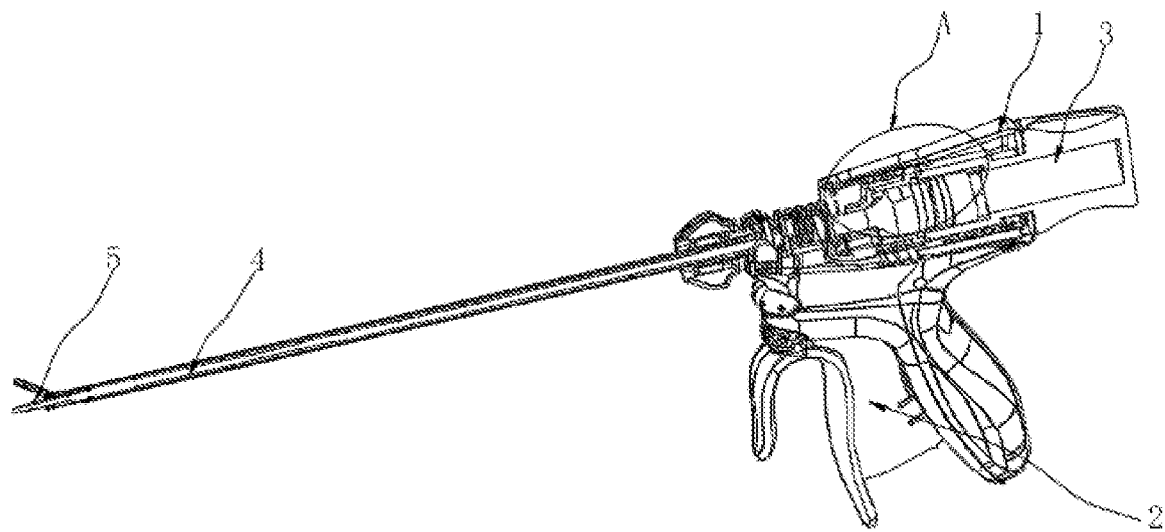
FIG. 3 is a structural sectional view of the disclosure.
Figure 6:
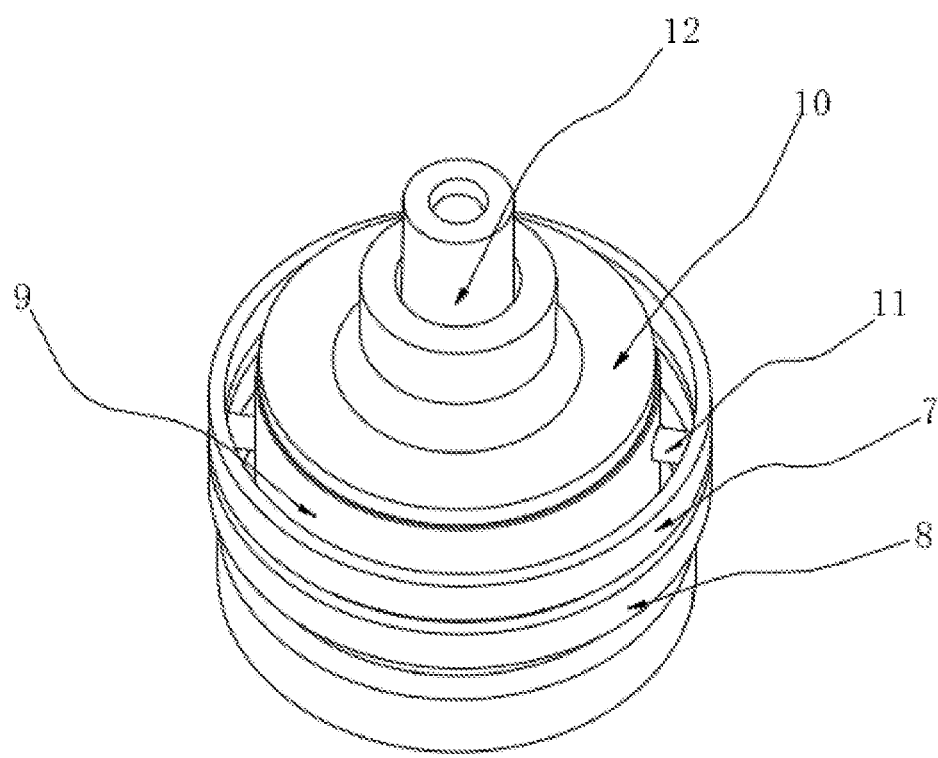
FIG. 6 is a partial internal structural view of the disclosure.

Referring to FIG. 2 and FIG. 6, the elastic conductive part 11 includes a spring needle or leaf spring for connecting the annular conductive part to the ultrasonic generator 12. By means of the spring needle or leaf spring, the connection between the annular conductive part and the ultrasonic generator 12 is facilitated, so that current output is facilitated.

Referring to FIG. 1, a handle 2 is arranged on an outer side of the scalpel body 1, and the handle 2 is configured for holding the scalpel body 1 by a hand, so as to ensure performability of the ultrasonic scalpel.

Figure 4:
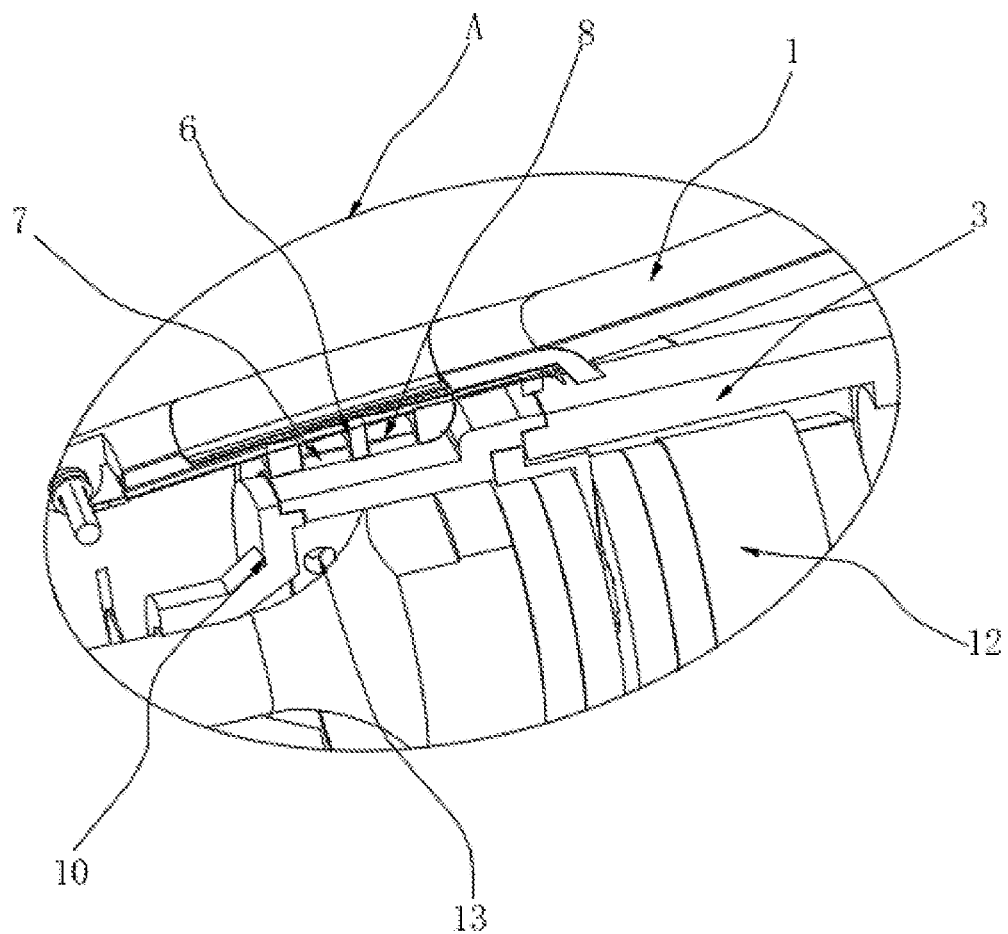
FIG. 4 is an enlarged view of part A in FIG. 3 of the disclosure.
Figure 5:
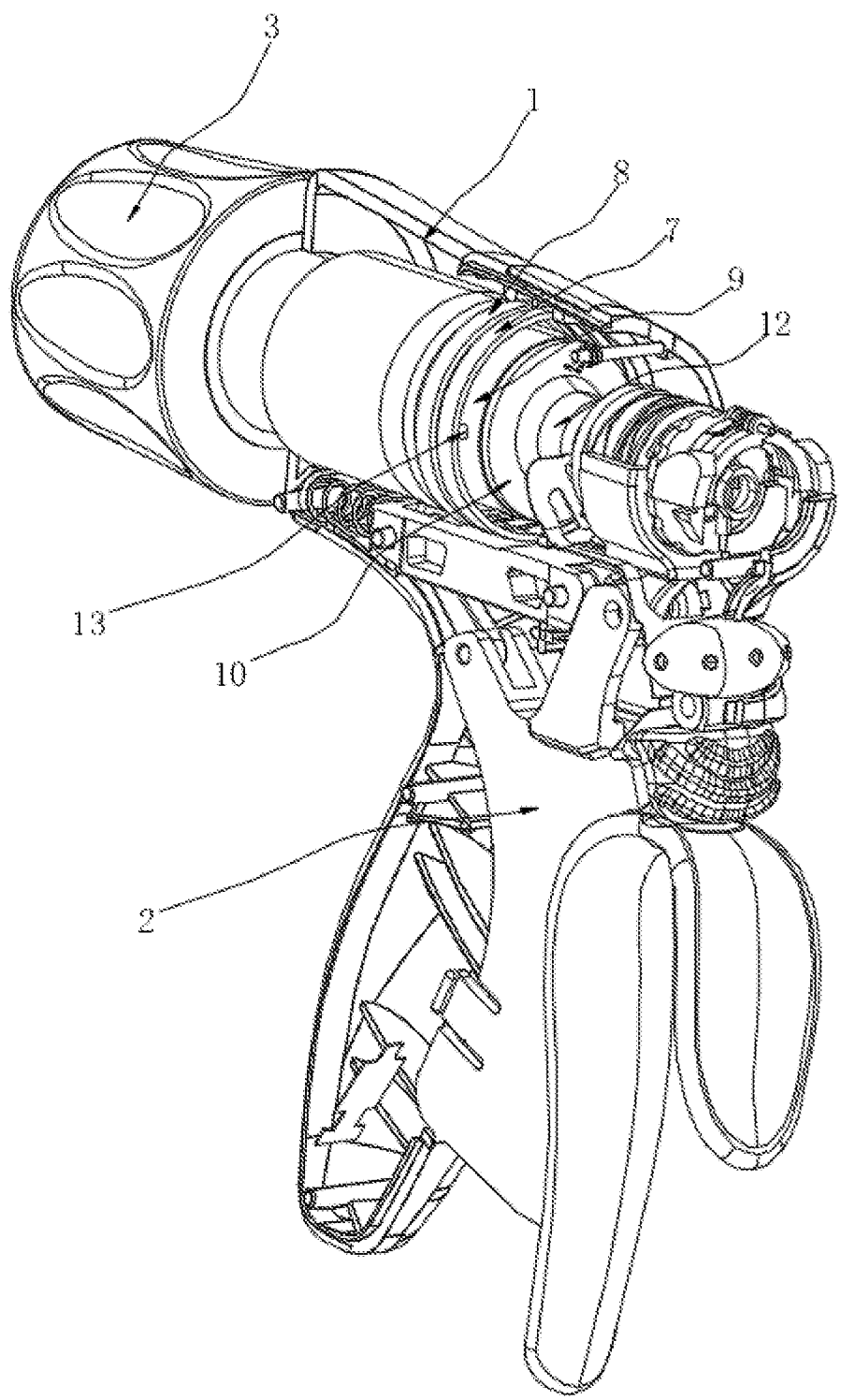
FIG. 5 is a partial structural sectional view of the disclosure.

Referring to FIG. 4 and FIG. 5, the mounting holes 13 which fit the elastic conductive part 11 are respectively provided in the outer side of the intermediate shell 9 to facilitate mounting of the elastic conductive part 11.

Referring to FIG. 2, the rear shell 3 and a front shell 10 which fit the ultrasonic generator 12 are arranged in the scalpel body 1. The rear shell 3 and the front shell 10 are configured for sealing the ultrasonic generator 12, so as to protect the ultrasonic generator 12, thereby prolonging the service life of the ultrasonic generator 12.

Referring to FIG. 4, a mounting groove which fits the ultrasonic generator 12 is provided in an inner wall of the intermediate shell 9. The mounting groove is configured for limiting the ultrasonic generator 12 to facilitate mounting of the ultrasonic generator 12, so as to limit radial motion of the ultrasonic generator 12, thereby ensuring normal operation of the ultrasonic scalpel.

Referring to FIG. 1, the scalpel blade 5 in cooperation with the handle 2 is arranged at a tail end of the scalpel rod 4. The scalpel blade 5 is electrically connected to the elastic conductive part 11 to facilitate better transmission from the ultrasonic generator 12 to the scalpel blade 5, so as to complete the task.

The operating principle of the disclosure is as follows: when in use, the ultrasonic generator 12 is assembled to the intermediate shell 9 via the mounting groove, such that the radial motion of the ultrasonic generator 12 is limited; and then the front shell 10 and the rear shell 3 are assembled, and are fixedly connected to the intermediate shell 9 by means of welding, bonding, or the like to limit relative axial motion of the ultrasonic generator 12, so as to seal the ultrasonic generator 12 to better protect the ultrasonic generator 12, thereby greatly prolonging the service life of the ultrasonic generator 12.

Afterwards, the positive and negative electrodes of the ultrasonic generator 12 are soldered to the elastic conductive part 11; then the elastic conductive part 11 penetrates through the intermediate shell 9 via the mounting holes 13 to be slidably connected to the annular conductive part respectively. Specifically, the spring needle or leaf spring penetrates through the mounting holes 13 to be connected to the first conductive ring 7 and the second conductive ring 8 respectively, and the external electric wires penetrate into the scalpel body 1 to be connected to the first conductive ring 7 and the second conductive ring 8. When an angle of the scalpel blade 5 needs to be adjusted, it is only necessary to rotate the rear shell 3, which is simple and rapid and prevents the external electric wires from being wound, so that the control degree of the operator is enhanced, thereby improving the success rate of the operation.

Although the embodiments of the disclosure have been shown and described, they are merely intended to illustrate the disclosure, rather than to limit the disclosure. The specific features, structures, materials or characteristics described may be combined in an appropriate manner in any one or more of the embodiments or examples. Upon reading the description, those having ordinary skills in the art can make modifications, substitutions, variations, and the like as required, which have no creative contribution to the embodiments, without departing from the principle and purpose of the disclosure. All the modifications, substitutions, variations, and the like are protected by the patent law as long as they are contained in the scope of the claims of the disclosure.

The invention claimed is:

1. An ultrasonic scalpel, comprising a scalpel body, a scalpel rod, and an ultrasonic generator, wherein an annular conductive part, the ultrasonic generator, and an elastic conductive part are arranged in the scalpel body; the scalpel rod is connected to an output terminal of the ultrasonic generator; the annular conductive part and the scalpel body are connected to each other; an intermediate shell is arranged to fixedly engage with an outer side of the ultrasonic generator; a mounting hole which fits the elastic conductive part is provided in an outer side of the intermediate shell; and the elastic conductive part is electrically connected to the ultrasonic generator and the annular conductive part, wherein the elastic conductive part penetrates through the intermediate shell via the mounting hole to be slidably connected to the annular conductive part.

2. The ultrasonic scalpel according to claim 1, wherein the annular conductive part comprises a first conductive ring and a second conductive ring; the scalpel body is internally provided with two clamping grooves in cooperation with the first conductive ring and the second conductive ring respectively.

3. The ultrasonic scalpel according to claim 1, wherein the elastic conductive part comprises a spring needle or leaf spring for connecting the annular conductive part to the ultrasonic generator.

4. The ultrasonic scalpel according to claim 1, wherein a handle is arranged on an outer side of the scalpel body; and the handle is configured for holding the scalpel body by a hand.

5. The ultrasonic scalpel according to claim 1, wherein a rear shell and a front shell which fit the ultrasonic generator are arranged in the scalpel body, and the rear shell and the front shell are both configured for sealing the ultrasonic generator.

6. The ultrasonic scalpel according to claim 5, wherein a scalpel blade in cooperation with a handle is arranged at a tail end of the scalpel rod, and the scalpel blade is electrically connected to the elastic conductive part.

7. The ultrasonic scalpel according to claim 1, wherein a mounting groove through which the ultrasonic generator is assembled to the intermediate shell is provided in an inner wall of the intermediate shell, and the mounting groove is configured to facilitate mounting of the ultrasonic generator, and configured for limiting a radial motion of the ultrasonic generator.

* * * * *